US006759193B2

(12) United States Patent
Oon et al.

(10) Patent No.: US 6,759,193 B2
(45) Date of Patent: *Jul. 6, 2004

(54) DETECTION OF HUMAN HEPATITIS B VIRUS SURFACE ANTIGEN MUTANTS BY SPECIFIC AMPLIFICATION AND ITS APPLICATION ON GENE CHIP

(75) Inventors: Chong-Jin Oon, Singapore (SG); Wei-Ning Chen, Singapore (SG); Ai-Lin Leong, Singapore (SG); Shiuan Koh, Singapore (SG)

(73) Assignee: The Government of the Republic of Singapore, Singapore (SG)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/362,394

(22) Filed: Jul. 28, 1999

(65) Prior Publication Data

US 2003/0003549 A1 Jan. 2, 2003

(51) Int. Cl.⁷ .............................. C12Q 1/68; C12Q 1/70; C12P 19/34
(52) U.S. Cl. .............................. 435/6; 435/5; 435/91.2; 536/23.72; 536/24.3; 536/24.33
(58) Field of Search .............................. 435/5, 6, 91.2; 536/23.72, 24.3, 24.33

(56) References Cited

U.S. PATENT DOCUMENTS

| | | | |
|---|---|---|---|
| 5,629,153 A | | 5/1997 | Urdea |
| 5,955,598 A | * | 9/1999 | Birkenmeyer et al. ... 536/24.33 |
| 6,100,030 A | * | 8/2000 | McCasky Feazel et al. .... 435/6 |

FOREIGN PATENT DOCUMENTS

| | | |
|---|---|---|
| EP | 0020251 | 12/1980 |
| WO | WO9313120 | 7/1993 |
| WO | WO9511307 | 4/1995 |
| WO | WO9640996 | 12/1996 |
| WO | WO 97/40193 | * 10/1997 |

OTHER PUBLICATIONS

Carman, W.F., et al., "Hepatitis B virus envelope variation after transplantation with and without hepatitis B immune globulin prophylaxis." *Hepatology* (1996), vol. 24, pp. 489–493. (Exhibit 1).
Goffeau, A., "Molecular fish on chips." *Nature* (1997), vol. 385, pp. 202–203. (Exhibit 2).
Guo, Z., et al., "Direct fluorescence analysis of genetic polymorphisms by hybridization with oligonucleotide arrays on glass supports." *Nucl. Acids Res.* (1994), vol. 22, pp. 5456–5465. (Exhibit 3).
Hoheisel, J., "Oligomer–chip technology." *Trends Biotechnol.* (1997), vol. 15, pp. 465–469. (Exhibit 4).

Hsu, H.Y., et al., "Surface gene mutants of hepatitis B virus in infants who develop acute or chronic infections despite immunoprophylaxis." *Hepatology* (1997), vol. 26, pp. 786–791. (Exhibit 5).
Marshall, A. and Hodgson, J., "DNA chips: an array of possibilities." *Nat. Biotechnol.* (1998), vol. 16, pp. 27–31. (Exhibit 6).
Ogata, N., et al., "Infectivity and pathogenecity in chimpanzees of a surface gene mutant of hepatitis B virus that emerged in a vaccinated infant." *J. Infect. Dis.* (1997), vol. 175, pp. 511–523. (Exhibit 7).
Oon, C.J. and Chen, W.N., "Current aspects of hepatitis B virus surface antigen mutants in Singapore." *J. Viral. Hepatitis* (1998), vol. 5(2), pp. 17–24. (Exhibit 8).
Oon, C.J., Chen, W.N., Koh, S., and Lim, G.K., "Identification of hepatitis B surface antigen variants with alterations outside the 'a' determinant in immunized Singapore infants." *J. Infect. Dis.* (1999), vol. 179(1), pp. 259–263. (Exhibit 9).
Oon, C.J., Chen, W.N., Zhao, Y., and Teng, S.W., "Detection of hepatitis B virus surface antigen mutants and their integration in human hepatocellular carcinoma." *Cancer Letters* (1999), vol. 136(1), pp. 95–99. (Exhibit 10).
Oon, C.J., Chen, W.N., Lim, N., Lim, G.K., Koh, S., Leong, A.L., Tan. G.S., and Teng, S.W., "Hepatitis B virus variants with lamivudine–related mutations in the DNA polymerase and the 'a' epitope of the surface antigen are sensitive to ganciclovir." *Antiviral Res.* (1999), vol. 41(3), pp. 113–118. (Exhibit 11).
Oon, C.J., et al., "Natural history of hepatitis B surface antigen mutants in children." *Lancet* (1996), vol. 348, pp. 1524–1525. (Exhibit 12).
Oon, C.J., et al., "Molecular epidemiology of hepatitis B virus vaccine variants in Singapore." *Vaccine* (1995), vol. 13, pp. 699–702. (Exhibit 12).
Saiki, R.K., et al., "Genetic analysis of amplified DNA with immobilized sequence–specific oligonucleotide probes." *Proc. Natl. Acad. USA* (1989), vol. 86, pp. 6230–6234. (Exhibit 14).
Yershov G., Barsky, V., et al., "DNA analysis and diagnostics on oligonucleotide microchips." *Proc. Natl. Acad. Sci. USA* (1996), vol. 93, pp. 4913–4918. (Exhibit 15).
Cariani, et al., (1995) "Emergence of Hepatitis Virus S Gene Mutant in a Liver Transplant Recipient", *Journal of Medical Virology*, 47: 410–415 (Exhibit 6).
Chiou, et al., (1997) "Altered Antigenicity of 'a' Determinant Variants of Hepatitis", *Journal of General Virology*, 78: 2639–2645. (Exhibit 7).

(List continued on next page.)

*Primary Examiner*—Donna C. Wortman
(74) *Attorney, Agent, or Firm*—John P. White; Cooper & Dunham LLP

(57) ABSTRACT

Novel DNA probe sequences for detection, by polymerase chain reaction, of human hepatitis B virus surface antigen mutant 145 (Glycine to Arginine) from serum samples. As a direct application, these specific DNA probes are immobilized on solid glass supports (gene chip) for detection of human hepatitis B virus surface antigen mutant 145 (Glycine to Arginine) by fluorescence.

36 Claims, 1 Drawing Sheet

OTHER PUBLICATIONS

Ireland, et al., (1999) "Reactivity of In Vitro Expressed Hepatitis B Surface Antigen Variants in Commercial Diagnostic Assays", Genbank NCBI Accession No. AF134137. (Exhibit 8).

Pult, et al., (1994) "Hepatitis B Virus Complete Genome With Insertion in Core Promoter, 198bp Insertion in X–ORF", Genbank NCBI Accession No. X98075. (Exhibit 9).

Pult, et al., (1997) "A Hepatitis B Virus Mutant With a New Hepatocyte Nuclear Factory 1 Binding Site Emerging in Transplant–Transmitted Fulminant Hepatitis B", *Hepatology*, 25: 1507–1515. (Exhibit 10); and.

Wands, et al., (1992) "Molecular Pathogenesis of Liver Disease During Persistent Hepatitis B Virus Infection", *Seminars in Liver Disease*, 12: 252–264. (Exhibit 11).

* cited by examiner

Figure 1. Detection of human hepatitis B virus surface antigen mutant 145 (Glycine to Arginine)

```
                           SEQUENCE LISTING

<160> NUMBER OF SEQ ID NOS: 9

<210> SEQ ID NO 1
<211> LENGTH: 14
<212> TYPE: DNA
<213> ORGANISM: Wild type human Hepatitis B virus

<400> SEQUENCE: 1
tacggacaga aact                                                         14

<210> SEQ ID NO 2
<211> LENGTH: 21
<212> TYPE: DNA
<213> ORGANISM: Wild type human Hepatitis B virus

<400> SEQUENCE: 2
ttagggttta aatctatacc c                                                 21

<210> SEQ ID NO 3
<211> LENGTH: 14
<212> TYPE: DNA
<213> ORGANISM: Wild type human Hepatitis B virus

<400> SEQUENCE: 3
tacggacgga aact                                                         14

<210> SEQ ID NO 4
<211> LENGTH: 27
<212> TYPE: DNA
<213> ORGANISM: Wild type human Hepatitis B virus

<400> SEQUENCE: 4
tacggacgga aactgttttt tttttt                                            27
```

```
<210> SEQ ID NO 5
<211> LENGTH: 27
<212> TYPE: DNA
<213> ORGANISM: Wild type human Hepatitis B virus

<400> SEQUENCE: 5
tacggacaga aactgttttt tttttttt                                           27

<210> SEQ ID NO 6
<211> LENGTH: 20
<212> TYPE: DNA
<213> ORGANISM: Wild type human Hepatitis B virus

<400> SEQUENCE: 6
aggatcaaca acaaccagta                                                    20

<210> SEQ ID NO 7
<211> LENGTH: 20
<212> TYPE: DNA
<213> ORGANISM: Wild type human Hepatitis B virus

<400> SEQUENCE: 7
atcgtcctgg gctttcgcaa                                                    20

<210> SEQ ID NO 8
<211> LENGTH: 35
<212> TYPE: DNA
<213> ORGANISM: Wild type human Hepatitis B virus

<400> SEQUENCE: 8
atgaattcat ggagagcaca acatcaggat tccta                                   35

<210> SEQ ID NO 9
<211> LENGTH: 35
<212> TYPE: DNA
<213> ORGANISM: Wild type human Hepatitis B virus

<400> SEQUENCE: 9
gagaattctc aaatgtatac ccaaagacaa aagaa                                   35
```

DETECTION OF HUMAN HEPATITIS B VIRUS SURFACE ANTIGEN MUTANTS BY SPECIFIC AMPLIFICATION AND ITS APPLICATION ON GENE CHIP

TECHNICAL FIELD

This invention relates to nucleic acid amplification with subsequent hybridization on solid supports (gene chip on glass support) as its application. More specifically, it relates to novel nucleic acid probes for detecting human hepatitis B virus surface antigen mutant 145 (Glycine to Arginine) in serum samples.

Throughout this invention, various publications are referenced by Arabic numerals. The disclosure of these publications is hereby incorporated by reference into this application to describe more fully the art to which this invention pertains.

BACKGROUND OF THE INVENTION

The present invention concerns the specific detection from serum samples of human hepatitis B virus surface antigen mutant 145 (Glycine to Arginine), by polymerase chain reaction, using novel nucleic acid probes. The present invention could be applied to detection of such mutant by other means, in particular detection of differential fluorescent signals after hybridization of unknown human viral DNA samples with a specific nucleic acid probe that is immobilized on solid supports (i.e. glass).

Viral hepatitis is a systemic disease involving primarily the liver, with hepatitis B virus being mainly responsible for most cases of acute or chronic hepatitis.

Antigenic characterization of human hepatitis B virus derives from the complex protein found on the virus' surface, namely hepatitis B virus surface antigen. The major antigenic epitope, designated as 'a' and located from amino acid 124 to 147 of the hepatitis B virus surface antigen, is common to all hepatitis B virus. This 'a' epitope is directly involved in inducing neutralizing antibodies against hepatitis B viral infection. Such induction can be achieved by immunizing individuals with commercial available vaccines, consisting of non-infectious subviral hepatitis B surface antigen particles. An acquired protection in humans against hepatitis B viral infection is generally indicated by the presence of an adequate amount of serum antibody to hepatitis B virus surface antigen (anti-HBs). There is also a concomitant decrease of the serum viral surface antigen. However, an increasing numbers of incidence of hepatitis B viral infection despite the serum anti-HBs have been reported. These are largely contributed by hepatitis B viral strains that carry mutations on the antigenic region of the viral surface antigen, and in particular on the 'a' epitope. Such surface antigen mutants are of serious concern as they display reduced affinity for the neutralizing antibodies and able to replicate independently. The most common mutation among these vaccine-escape hepatitis B virus variants has been found at amino acid residue 145 (Glycine to Arginine) on the 'a' epitope of the viral surface antigen. In immunized infants born to HBeAg positive mothers, for example, the mutation 145 (Glycine to Arginine) within the major hydrophilic region is the most common variant found in those who subsequently become infected despite adequate amount of protective anti-HBs antibodies. This particular mutant is also the most common variant found in orthotopic liver transplantation patients who succumbed to hepatitis B viral infection despite immunoprophylaxis using hepatitis B immunoglobulin. Significantly, this human hepatitis B virus surface antigen mutant 145 (Glycine to Arginine) is also a naturally occurring variant that has been detected worldwide. In Singapore, despite the fact that an active vaccination program has resulted in a significant decrease of acute hepatitis B infection and the incidence of primary hepatocellular carcinoma in the general population, cases of breakthrough viral infection have been detected. Many of them (twelve out of forty-one) carry the viral surface antigen mutation 145 (Glycine to Arginine).

The emergence of this replicative hepatitis B virus surface antigen mutant 145 (Glycine to Arginine) and its ability to escape detection using currently available reagents are of grave concern, because this mutant is infectious and has resulted in the development of acute hepatitis B in Europe as well as Singapore. Our latest data also point to an increasing incidence of quasispecies in Singapore population consisting of both wild type and surface antigen 145 (Glycine to Arginine) of hepatitis B virus. Although serum human hepatitis B viral DNA can be detected by standard liquid hybridization assay (Abbott Laboratories, U.S.A.), such commercial kits are not designed to distinguish wild type hepatitis B virus from variants carrying mutations on hepatitis B surface antigen. A rapid and simple detection method for this particular human hepatitis B virus surface antigen mutant 145 (Glycine to Arginine) would therefore be useful for its diagnosis, therapy and prevention.

One approach toward this goal would be to detect the specific nucleic acid sequence of the HBsAg mutant 145 (Glycine to Arginine) in serum samples by specific Polymerase Chain Reaction amplification. Specific oligonucleotides would need to be designed on the basis of various available HBsAg sequences. Current methods of nucleic acid and oligonucleotide identifications have problems of sensitivity and selectivity, and have disadvantages such as the tedious and cumbersome analysis of the amplification results requiring highly skill operators to carry out the analyses i.e. agarose gel, polyacrylamide gel and molecular cloning. Application by the sophisticated oligonucleotide-based chip (Gene Chip) technology can provide further improved accuracy and rapid diagnostic screening assay. Gene Chip technology is now making more efficient and easier to use tools possible for obtaining and evaluating genetic information. This technology can be used for a broad spectrum of applications and analysis, such as sequence analysis, genotyping and monitoring of gene expression.

First developed in the late 1980s as a concept to determining DNA sequence by hybridization, the Gene Chip technology has been used in various fields of medicine and pharmaceutical research. Usually immobilized on solid support such as glass, the probe sequences can be originated from different procedures. These include the photolithographic synthesis of 20–25-mer oligonucleotides onto silicon wafers (Affymetrix, Glaxo-Welcome), printing of 500–5000 nucleotide cDNAs onto glass chip or dotting of pre-synthesized specific oligonucleotides (via their chemically modified terminus) onto glass chip. For the purpose of detecting hepatitis B surface antigen mutants with high specificity, the limited number of possible mutation sites (amino acid 100–160) would favor the dotting of pre-made oligonucleotides onto glass support in the application of Gene Chip technology. A specific detection system for hepatitis B surface antigen Glycine-145-Arginine mutant has been developed and described in this disclosure. It is based on novel nucleic acid probes which constitute an important innovative step towards the goals mentioned. Their identification would contribute to the effective prevention and control of hepatitis B viral infection arising from these viral surface antigen mutants, through rapid screening in blood banks, commercial and research diagnostic laboratories. This know-how information can also be used to detect other hepatitis B mutants.

The specific detection system described in the present invention that is based on novel nucleic acid probes constitutes an important step towards these goals and should contribute to the effective control of hepatitis B viral infection arising from these viral surface antigen mutants.

SUMMARY OF THE INVENTION

This invention describes novel nucleic acid probes that can be used in polymerase chain reaction to amplify specifically human hepatitis B surface antigen mutant 145 (Glycine to Arginine) from serum samples. In contrast to commercial liquid hybridization assays, the detection system in the present invention is able to detect the said human hepatitis B viral mutant from serum samples with specificity. The specificity of the present invention in turn allows detection of such mutant using gene chip technology, wherein the specific fluorescent labeled nucleic acid probe is immobilized on solid glass supports prior to hybridization reaction with target viral DNA fragment labeled by different fluorescent dye, and amplified from serum samples. The specific detection of this infectious human vaccine-escape hepatitis B surface antigen mutant 145 (Glycine to Arginine), from quasispecies serum samples, provides useful information for future monitoring of such mutants using specific therapeutic vaccines and effective antiviral agents.

BRIEF DESCRIPTION OF THE FIGURE

FIG. 1 is a photograph that shows electrophoresis pattern of the polymerase chain reaction product using either plasmid or viral DNA as template. The plasmid is pcDNA3.1 (InvitroGen, U.S.A.) containing the coding region of the human hepatitis B virus surface antigen, either the wild type (lane 1) or the mutant 145 (Glycine to Arginine) (lane 2). The viral DNA is isolated from serum samples containing either the wild type (lane 3) or mutant 145 (Glycine to Arginine) (lane 4) human hepatitis B virus. Human hepatitis B virus DNA is extracted from serum sample by phenol/chloroform. Polymerase chain reaction amplification is carried out in the present invention using specific oligonucleotides.

DETAILED DESCRIPTION OF THE INVENTION

This invention provides a method for detecting specifically from serum samples the human hepatitis B virus surface antigen mutant 145 (Glycine to Arginine), by polymerase chain reaction. Direct application of this detection system includes the detection of human hepatitis B virus surface antigen mutant 145 (Glycine to Arginine) by detecting differential fluorescent signals, following hybridization of human hepatitis viral DNA with novel nucleic acid probes immobilized on solid glass supports.

The subject matter of the present invention is the development of a simple, sensitive method to detect human hepatitis B virus surface antigen mutant 145 (Glycine to Arginine) from serum samples. As a direct application, detection of this particular mutant could be achieved by detecting differential fluorescent signals after hybridization of the novel nucleic acid probes immobilized on solid glass supports and target viral DNA sequences.

The present invention consists of the design of novel oligonucleotides that can be used in polymerase chain reaction, to specifically amplify the human hepatitis B virus surface antigen mutant 145 (Glycine to Arginine). A set of synthetic oligonucleotides useful as amplifier probes, comprise at least two different oligonucleotides probes, wherein each oligonucleotide probe consisting of:

1. first oligonucleotide having 14 nucleotides (5'-TACGGACAGAAACT-3'(SEQ ID no:1), position 582 to 595 as referred to the wild type human hepatitis B virus genome) which contains the mutation G to A, leading to change at amino acid 145 of hepatitis B virus surface antigen (Glycine to Arginine), at position 8 of the oligonucleotide;
2. second oligonucleotide having 21 nucleotides (5'-TTAGGGTTTAAATCTATACCC-3'(SEQ ID no:2), position 842 to 822 as referred to the wild type human hepatitis B virus genome), which is complementary to the coding strand of hepatitis B virus surface antigen Further subject matters of the present invention include reagents for implementing the method, namely the viral DNA extraction from human serum samples, the polymerase chain reaction.

One of the applications of the present invention is the detection of the human hepatitis B virus surface antigen mutant 145 (Glycine to Arginine) using a solid glass supports device. In the present invention, further modifications have been added to two oligonucleotides (listed herein): 5'-TACGGACGGAAACT-3'(SEQ ID NO:3), and 5'-TACGGACAGAAACT-3'(SEQ ID NO:1), both located from position 582 to 595 as referred to the wild type human hepatitis B virus genome. These modifications include a fluorescent dye, 6-(fluorescein-6-carboxamido) hexanoate (6 FAM), at its 5' terminus and a primary amine group at its 3' terminus. The resulting oligonucleotides that are immobilized on solid glass supports have the following structure: 5'-(6 FAM) TACGGACGGAAACTGTTTTTTTTTTTT (C-7 amine)-3'(SEQ ID NO:4), and 5'-(6 FAM) TACGGACAGAAACTGTTTTTT TTTTTTT (C-7 amine)-3'(SEQ ID NO:5), and the second oligonucleotide contains the mutation G to A (position 8) leading to change at amino acid 145 (Glycine to Arginine) of human hepatitis B virus surface antigen. There is also an inclusion of a poly-T (underlined) as a synthetic linker aiming at facilitating the subsequent hybridization reaction with target human viral DNA sequences from serum samples.

The present invention also concerns the design of synthetic oligonucleotides that can be used to amplify target human hepatitis B virus surface antigen DNA from serum samples, prior to their hybridization with the oligonucleotide immobilized on solid glass supports as mentioned above. Specifically, these oligonucleotides used in polymerase chain reaction to generate amplified product of less than 150 base pairs and consist of the following structure:

1. first oligonucleotide having 20 nucleotides with a biotin group at its 5' terminus (5'-Biotin-AGGATCAACAACAACCAGTA-3'(SEQ ID no:6), and located from position 489 to 508 as referred to the wild type human hepatitis B virus genome). The presence of a biotin group allows the separation of amplified DNA fragments using streptavidin magnetic particles;
2. second oligonucleotide having 20 nucleotides with a fluorescent dye Texas Red at its 5' terminus, and complementary to the coding strand of human hepatitis B virus surface antigen (5'-Texas red-ATCGTCCTGGGCTTTCGCAA-3'(SEQ ID no:7), and located from position 634 to 615 as referred to the wild type human hepatitis B virus genome).

In accordance with the present invention, serum samples may contain the human hepatitis B virus surface antigen mutant 145 (Glycine to Arginine). The present invention enables its specific detection. For detection by means other than visualizing human hepatitis B viral surface antigen mutant 145 (Glycine to Arginine) DNA fragments, the present invention can be further developed into gene chip whereby the oligonucleotide used in specific amplification of the said hepatitis B viral mutant is immobilized onto solid glass supports. The presence of the human hepatitis B virus surface antigen mutant 145 (Glycine to Arginine) in a particular serum samples can be detected by fluorescence signals upon hybridization with the immobilized oligonucleotide.

Examples of applications of the present invention are shown below, however, the present invention shall in no way be limited to these examples.

EXAMPLES

General Experimental Procedures

Viral DNA from serum carrying either the wild type or mutant 145 (Glycine to Arginine) of the human hepatitis B virus surface antigen is isolated as follows. 200 µl of the serum sample was added to 400 µl of lysis buffer (Tris chloride 10 mM, pH 7.4, EDTA 1 mM, and sodium dodecyl sulfate 2%) and 25 µl of proteinase K (20 mg/ml), incubated at 65° C. for 3 hours. Viral DNA is then extracted by phenol/chloroform and precipitated by ethanol.

The coding region of the human hepatitis B virus surface antigen, either wild type or mutant 145 (Glycine to Arginine), is amplified by polymerase chain reaction using the following oligonucleotides:

1. The 5' oligonucleotide is a sense oligonucleotide that matches the start site of the human hepatitis B surface antigen (5'-ATGAATTCATGGAGAGCACAACAT CAGGATTCCTA-3'(SEQ ID no:8), and located from position 157 to 183 as referred to the wild type human hepatitis B viral genome), wherein the underlined nucleotides represent an additional site for restriction enzyme EcoRI;
2. The 3' oligonucleotide is an anti-sense oligonucleotide that matches the stop site of the human hepatitis B surface antigen (5'-GAGAATTCTCAAATGTATACCCAAAGAC AAAAGAA-3'(SEQ ID no:9), located from position 811 to 837 as referred to the wild type human hepatitis B viral genome), wherein the underlined nucleotides represent an additional site for restriction enzyme EcoRI;

Polymerase chain reaction using viral DNA as template is then carried out on a DNA Thermal Cycler (Perkin-Elmer, Cetus) for 35 cycles using Pfu polymerase (Stratagene, U.S.A.). Cycling conditions consist of 1.5 minutes at denaturing temperature (94° C.), 2 minutes at annealing temperature (53° C.) and 2 minutes at extension temperature (72° C.).

Amplified viral DNA fragment (human hepatitis B virus surface antigen, either wild type or mutant 145 (Glycine to Arginine)) is subjected to restriction enzyme by EcoRI, prior to cloning into pcDNA3.1 plasmid (InvitroGene, U.S.A.) pretreated by the same restriction enzyme.

For the novel detection system in the present invention, polymerase chain reaction is carried out using either plasmid DNA (containing coding region of either wild type or mutant 145 (Glycine to Arginine) of human hepatitis B virus surface antigen), or viral DNA as indicated in FIG. 1. Oligonucleotides used in the said polymerase chain reaction are listed herein and have the following localization on the wild type human hepatitis B viral genome:

1. the 5' oligonucleotide having 14 nucleotides (5'-TACGGACAGAAACT-3')(SEQ ID no:1) covers positions 582 to 595.

Specifically, it contains the mutation G to A at position 8 of the said oligonucleotide, leading to change at amino acid 145 (Glycine to Arginine) of the human hepatitis B virus surface antigen;

2. the 3' oligonucleotide having 21 nucleotides (5'-TTAGGGTTTAAATCTATACCC-3')(SEQ ID no:2) covers positions 842 to 822. Specifically, it is an anti-sense oligonucleotide that is complementary to the coding strand of human hepatitis B virus surface antigen.

Cycling conditions of polymerase chain reaction using the above-mentioned oligonucleotides are as follows: 1.5 minutes at denaturing temperature (94° C.), 2 minutes at annealing temperature (50° C.) and 2 minutes at extension temperature (72° C.). Amplified product is visualized after electrophoresis on an 2% agarose gel. A total of 35 cycles using Pfu polymerase (Stratagene, U.S.A.) generate an amplified product of expected size (240 base pairs) for plasmid (lane 2 in FIG. 1) and viral DNA (lane 4 in FIG. 1) carrying human hepatitis B virus surface antigen mutant 145 (Glycine to Arginine). The specificity of the detection system in the present invention is indicated by the absence of amplified product using templates carrying the wild type human hepatitis B virus surface antigen (plasmid template in lane 1, and viral DNA in lane 3 of the FIG. 1). The said specificity is further supported by the absence of amplified product using templates carrying mutations leading to amino acid changes at position 126, 129 and 133 of the human hepatitis B virus surface antigen.

Example 1

Detection of human hepatitis B virus surface antigen mutant 145 (Glycine to Arginine) on solid glass supports (Gene Chip)

An increasing number of human hepatitis B virus mutants are being identified. Whereas some of them derive from random variations during viral replication cycles, many others emerge from selection pressure such as immunoprophylaxis with vaccines and therapeutic treatment with antiviral drugs. These 'escape' mutants are of concern as they are generally replicative and some can be infectious leading to acute liver diseases. Identification of such human hepatitis B virus mutants from serum samples is therefore of great importance. One of the most powerful approaches would be a differential amplification by mutation-specific oligonucleotide probes, as described in the present invention. With appropriate selection of oligonucleotide and amplification conditions, our novel detection system in the present invention allows the discrimination between a target human hepatitis B virus and the said mutant 145 (Glycine to Arginine) by only a single base. However, the manual and laborious gel-based analysis of amplified products could comprise its use in routine detection of the increasing numbers of human hepatitis B virus mutants, in particular those carrying mutations on the antigenic 'a' epitope of the viral surface antigen.

A promising alternative approach to this problem would be the development of analytical device that allows the simultaneous detection of different mutations, such as an array of hundreds or thousands of immobilized oligonucleotides (gene chip). In the case of human hepatitis B virus surface antigen, solid glass supports with immobilized oligonucleotides that carry specific mutations would allow their simple and rapid detection.

As a direct application of the novel detection system in the present invention, modifications have been added to two oligonucleotides (listed herein): 5'-TACGGACGGAAACT-3 (SEQ ID NO:3), and 5'-TACGGACAGAAACT-3"(SEQ ID NO:1), both located from position 582 to 595 as referred to the wild type human hepatitis B virus genome. These include a fluorescent dye, 6-(fluorescein-6-carboxamido) hexanoate, at its 5' terminus for microscopic detection and a primary amine group at its 3' terminus allowing its immobilization on solid glass supports. The resulting oligonucleotides that are immobilized on solid glass supports has the following structure: 5'-(6 FAM) TACGGACGGAAACTGTTTTTTTTTTTT (C-7 amine)-3'(SEQ ID NO:4), and 5'-(6 FAM) TACGGACAGAAACTGTTTTTTTTTTTT (C-7 amine)-3'(SEQ ID NO:5), and the second oligonucleotide contains the mutation G to A (position 8 of the oligonucleotide, in bold) leading to change at amino acid 145 (Glycine to Arginine) of human hepatitis B virus surface antigen. There is also an inclusion of a poly-T (underlined) as a synthetic linker aiming at optimizing the subsequent hybridization reaction with target human viral DNA sequences from serum samples.

Activation of Glass Slides

The said modified oligonucleotides are then immobilized on solid glass supports that are activated as follows:

immerse glass slides in 1% 3-aminopropyltrimethoxysilane solution in 95% acetone/water for 2 minutes;

wash glass slides in acetone;

dry glass slides at 100° C. for 45 minutes;

incubate glass slides in 0.2% 1-4-phenylene diisothiocyanate in 10% pyridine/dimethyl formamide for 2 hours;

wash glass slides with methanol and acetone;

store glass slides in vacuum desiccator.

Immobilization of Oligonucleotides the oligonucleotides:

1. oligonucleotide having 27 nucleotides with a fluorescent dye, 6-(fluorescein-6-carboxamido) hexanoate (6 FAM), at its 5' terminus and a primary amine group at its 3' terminus: 5'-(6 FAM) TACGGACGGAAACTGTTTTTTTTTTTT (C-7amine)-3' (SEQ ID no:4); and
2. oligonucleotide having 27 nucleotides with a fluorescent dye, 6-(fluorescein-6-carboxamido) hexanoate (6 FAM), at its 5' terminus and a primary amine group at its 3' terminus: 5'-(6 FAM) TACGGACAGAAACTGTTTTTTTTTTTT (C-7 amine)-3'(SEQ ID no:5)

are dissolved in 100 mM $Na_2CO_3$ (pH 9.0) to a final concentration of 20 nM;

apply 2 μl of the above solution containing oligonucleotides to the activated glass slides;

incubate glass slides with immobilized oligonucleotides at 37° C. for 2 hours in a humid chamber;

wash glass slides in 1% $NH_4OH$ and water, allow air dry at ambient temperature.

Amplification of Target Viral DNA

Specific oligonucleotides that can be used to amplify target human hepatitis B virus surface antigen DNA from serum samples are designed, prior to their hybridization with the oligonucleotide immobilized on solid glass supports as mentioned above. Specifically, these oligonucleotides consist of the following structure:

first oligonucleotide having 20 nucleotides with a biotin group at its 5' terminus (5'-Biotin-AGGATCAACAACAACCAGTA-3'(SEQ ID no:6), and located from position 489 to 508 as referred to the wild type human hepatitis B virus genome). The presence of a biotin group allows the separation of amplified DNA fragments using streptavidin magnetic particles;

second oligonucleotide having 20 nucleotides with a fluorescent dye Texas Red at its 5' terminus, and complementary to the coding strand of human hepatitis B virus surface antigen (5'-Texas red-ATCGTCCTGGGCTTTCGCAA-3')(SEQ ID no:7), and is located from position 634 to 615 as referred to the wild type human hepatitis B virus genome;

polymerase chain reaction is carried out using viral DNA (either wild type or mutant 145 with Glycine to Arginine mutation of human hepatitis B virus surface antigen) from serum samples as template, and generates an amplified product of 150 base pairs;

separate double stranded amplification product by immobilizing the biotinylated coding strand onto streptavidin magnetic particles;

solution containing single-stranded DNA with Texas Red fluorescent label is collected for subsequent hybridization with immobilized oligonucleotides.

Hybridization and Detection of Fluorescent Signals apply hybridization solution containing 50 nM Texas Red-labeled target single stranded DNA, 5×SSPE (NaCl, $NaH_2PO_4$, and EDTA) and 0.5% SDS (Sodium Dodecyl Sulfate) to glass slides carrying immobilized oligonucleotides at 30° C. for 3 hours;

wash with 2×SSPE and 0.1% SDS;

apply 50 μl of the above washing buffer to solid glass supports, cover with cover slips and detect fluorescence signals under fluorescent microscope.

Detection of fluorescence signals under microscope indicates a specific hybridization between the immobilized oligonucleotide: 5'-(6 FAM)TACGGACAGAAACTG TTTTTTTTTTTT (C-7 amine)-3'(SEQ ID no:5), with the G to A mutation (leading to Glycine to Arginine mutation at amino acid 145 of human hepatitis B virus surface antigen) and the target viral DNA carrying the same mutation. Conversely, specific hybridization occurs exclusively between the immobilized wild type oligonucleotide, 5'-(6 FAM)TACGGACGGAAACTGTTTTTTTTTTTT (C-7 amine)-3'(SEQ ID no:4), and the target viral DNA amplified from wild type human hepatitis B virus.

The present invention is based on a simple and specific system to detect human hepatitis B virus surface antigen mutant 145 (Glycine to Arginine) from serum samples. This specific detection provides useful information for further monitoring of this particular mutant. The successful application of this detection system onto solid glass supports makes fast and specific detection of the said human hepatitis B viral mutant at large scale possible. The detection system in the present invention can also be extended to other human hepatitis B viral mutants, including those emerged from selection pressure (either vaccine-based or therapeutic drug-based).

Further variations and modifications of the present invention will become apparent subsequently and are to be covered by the claims included in the present invention.

OTHER PUBLICATIONS

Carman, W. F., et al. "Hepatitis B virus envelope variation after transplantation with and without hepatitis B immune globulin prophylaxis", *Hepatoloqy* (1996), vol. 24, pp. 489–493.

Guo. Z., et al. "Direct fluorescence analysis of genetic polymorphisms by hybridization with oligonucleotide arrays on glass supports", *Nucl. Acids Res.* (1994), vol. 22, pp. 5456–5465.

Hoheisel J. Oligomer-chip technology. *Trends Biotechnol.* (1997), vol. 15, pp. 465–469.

Goffeau, A., "Molecular fish on chips", *Nature* (1997), vol. 385, pp. 202–203.

Hsu, H. Y., et al. "Surface gene mutants of hepatitis B virus in infants who develop acute or chronic infections despite immunoprophylaxis", *Hepatology* (1997), vol. 26, pp. 786–791.

Marshall A. and Hodgson J. "DNA chips: an array of possibilities." *Nat. Biotechnol.* (1998), vol. 16, pp. 27–31.

Ogata, N., et al. "Infectivity and pathogenicity in chimpanzees of a surface gene mutant of hepatitis B virus that emerged in a vaccinated infant", *J. Infect. Dis.* (1997), vol. 175, pp. 511–523.

Oon, C. J. "Evolution and transmission of hepatitis B virus mutants", Asian Pacific Hepatitis B Virus, *J. Royal College Phys.* (1997), London (ed. Zuckerman A. J.), pp. 177–190.

Oon, C. J. and Chen, W. N. "Current aspects of hepatitis B virus surface antigen mutants in Singapore. *J. Viral. Hepatitis* (1998), vol. 5(2), pp. 17–24.

Oon, C. J., Chen, W. N., Koh S., and Lim G. K. "Identification of hepatitis B surface antigen variants with alterations outside the 'a' determinant in immunized Singapore infants." *J. Infect. Dis.* (1999), vol. 179(1), pp. 259–263.

Oon, C. J., Chen, W. N., Zhao Y., Teng S. W. "Detection of hepatitis B virus surface antigen mutants and their integration in human hepatocellular carcinoma." *Cancer Letters* (1999), vol. 136(1), pp. 95–99.

Oon, C. J., Chen W. N., Lim N., Lim G. K., Koh S., Leong A. L., Tan G. S., and Teng S. W. "Hepatitis B virus variants with lamivudine-related mutations in the DNA polymerase and the 'a' epitope of the surface antigen are sensitive to ganciclovir." *Antiviral Res.* (1999), vol. 41(3), pp. 113–118.

Oon, C. J., et al. "Natural history of hepatitis B surface antigen mutants in children", *Lancet* (1996), vol. 348, pp. 1524–1525.

Oon, C. J., et al. "Molecular epidemiology of hepatitis B virus vaccine variants in Singapore", *Vaccine* (1995), vol. 13, pp. 699–702.

Saiki R. K., et. al. "Genetic analysis of amplified DNA with immobilized sequence-specific oligonucleotide probes." *Proc. Natl. Acad. USA* (1989), vol. 86, pp. 6230–6234.

Yershov G., Barsky V. et. al. "DNA analysis and diagnostics on oligonucleotide microchips." *Proc. Natl. Acad. Sci. USA* (1996), vol. 93, pp. 4913–4918.

What is claimed is:

1. An oligonucleotide which (1) is immobilized, (2) consists of the sequence TACGGACGGAAACT (SEQ ID NO:3), (3) is linked to a fluorescent dye at its 5' terminus, and (4) is linked to a primary amine group at its 3' terminus.

2. An oligonucleotide which (1) is immobilized, (2) consists of the sequence TACGGACGGAAACT-GTTTTTTTTTTTT (SEQ ID NO:4), (3) is linked to a fluorescent dye at its 5' terminus, and (4) is linked to a primary amine group at its 3' terminus.

3. The oligonucleotide of claim 1 or 2, wherein the fluorescent dye is 6-(fluorescein-6-carboxamido)hexanoate.

4. The oligonucleotide of claim 1 or 2, wherein the primary amine group is a C-7 amine.

5. The oligonucleotide of claim 1 or 2, wherein the oligonucleotide is immobilized on a solid support.

6. The oligonucleotide of claim 5, wherein the solid support is a glass bead.

7. An oligonucleotide which (1) is immobilized, (2) consists of the sequence TACGGACAGAAACT (SEQ ID NO:1), (3) is linked to a fluorescent dye at its 5' terminus, and (4) is linked to a primary amine group at its 3' terminus.

8. An oligonucleotide which (1) is immobilized; (2) consists of the sequence TACGGACAGAAACT-GTTTTTTTTTTTT (SEQ ID NO:5), (3) is linked to a fluorescent dye at its 5' terminus, and (4) is linked to a primary amine group at its 3' terminus.

9. The oligonucleotide of claim 7 or 8, wherein the fluorescent dye is 6-(fluorescein-6-carboxamido)hexanoate.

10. The oligonucleotide of claim 7 or 8, wherein the primary amine group is a C-7 amine.

11. The oligonucleotide of claim 7 or 8, wherein the oligonucleotide is immobilized on a solid support.

12. The oligonucleotide of claim 11, wherein the solid support is a glass bead.

13. An oligonucleotide which (1) has a sequence which corresponds to a portion of a nucleic acid which encodes human hepatitis B virus surface antigen, wherein the sequence is AGGATCAACAACAACCAGTA (SEQ ID NO:6), and (2) is linked at its 5' terminus to a biotin group.

14. An oligonucleotide which (1) consists of the sequence ATCGTCCTGGGCTTTCGCAA (SEQ ID NO:7), and (2) is linked at its 5' terminus to a fluorescent dye.

15. The oligonucleotide of claim 14, wherein the fluorescent dye is Texas red.

16. A composition which comprises a first oligonucleotide and a second oligonucleotide, wherein:

(a) the first oligonucleotide (1) consists of the sequence AGGATCAACAACAACCAGTA (SEQ ID NO:6), and (2) is linked at its 5' terminus to a biotin group; and (b) the second oligonucleotide (1) consists of the sequence ATCGTCCTGGGCTTTCGCAA (SEQ ID NO:7), and (2) is linked at its 5' terminus to a Texas red fluorescent dye.

17. A method for identifying a human hepatitis B virus surface antigen mutant 145 in a sample which comprises:

(A) obtaining a viral nucleic acid from the sample;

(B) amplifying the viral nucleic acid in a polymerase chain reaction using two primers, wherein
    (1) one primer is a first oligonucleotide which (i) consists of the sequence AGGATCAACAACAAC-CAGTA (SEQ ID NO:6), and (ii) is linked at its 5' terminus to a biotin group; and
    (2) the other primer is a second oligonucleotide which (i) consists of the sequence ATCGTC-CTGGGCTTTCGCAA (SEQ ID NO:7), and (ii) is linked at its 5' terminus to a fluorescent dye;

(C) obtaining, from the amplified nucleic acid, single stranded nucleic acid which comprises the fluorescent dye; and (D) contacting the single stranded nucleic acid which comprises the fluorescent dye to an immobilized third oligonucleotide, which oligonucleotide comprises a sequence which (i) corresponds to a portion of a human hepatitis B virus surface antigen nucleic acid, which portion comprises a mutation present at the amino acid at position 145 of human hepatitis B virus surface antigen, (ii) is linked to a fluorescent dye at its 5' terminus, and (iii) is linked to a primary amine group at its 3' terminus, under conditions permitting hybridization between the single stranded nucleic acid which comprises the fluorescent dye and the third oligonucleotide, wherein hybridization between the single stranded nucleic acid which comprises the fluorescent dye and the immobilized third oligonucleotide identifies the sample as one containing a human hepatitis B virus surface antigen mutant 145.

18. The method of claim 17, wherein the third oligonucleotide comprises the sequence TACGGACAGAAACT (SEQ ID NO:1).

19. The method of claim 17, wherein the third oligonucleotide comprises the sequence TACGGACAGAAACT-GTTTTTTTTTTT (SEQ ID NO:5).

20. The method of claim 17, wherein the fluorescent dye which is linked to the third oligonucleotide is 6-(fluorescein-6-carboxamido) hexanoate.

21. The method of claim 17, wherein the primary amine group which is linked to the third oligonucleotide is a C-7 amine.

22. The method of claim 17, wherein the third oligonucleotide is immobilized on a solid support.

23. The method of claim 22, wherein the solid support is a glass bead.

24. The method of claim 17, wherein the third oligonucleotide (1) is immobilized; (2) comprises the sequence TACG-GACAGAAACTGTTTTTTTTTTT (SEQ ID NO:5), (3) is linked to 6-(fluorescein-6-carboxamido) hexanoate at its 5' terminus, and (4) is linked to a C-7 amine at its 3' terminus.

25. The method of claim 17, wherein the fluorescent dye which is linked to the primer in step (B) (2) is Texas red.

26. The method of claim 25, wherein the sample is a serum sample.

27. A method for identifying a wildtype human hepatitis B virus surface antigen in a sample which comprises:

(A) obtaining a viral nucleic acid from the sample;

(B) amplifying the viral nucleic acid in a polymerase chain reaction using two primers, wherein
    (1) one primer is a first oligonucleotide which (i) consists of the sequence AGGATCAACAACAAC-CAGTA (SEQ ID NO:6), and (ii) is linked at its 5' terminus to a biotin group; and
    (2) the other primer is a second oligonucleotide which (1) consists of the sequence ATCGTC-CTGGGCTTTCGCAA (SEQ ID NO:7), and (2) is linked at its 5' terminus to a fluorescent dye;

(C) obtaining, from the amplified nucleic acid, single stranded nucleic acid which comprises the fluorescent dye; and (D) contacting the single stranded nucleic acid which comprises the fluorescent dye to an immobilized third oligonucleotide, which oligonucleotide comprises a sequence which (1) corresponds to a portion of a wildtype human hepatitis B virus surface antigen nucleic acid, (2) is linked to a fluorescent dye at its 5' terminus; and (3) is linked to a primary amine group at its 3' terminus, under conditions permitting hybridization between the single stranded nucleic acid which comprises the fluorescent dye and the third oligonucleotide, wherein hybridization between the single stranded nucleic acid which comprises the fluorescent dye and the third oligonucleotide identifies the sample as one containing a wildtype human hepatitis B virus surface antigen.

28. The method of claim 27, wherein the third oligonucleotide comprises the sequence TACGGACGGAAACT (SEQ ID NO:3).

29. The method of claim 27, wherein the third oligonucleotide comprises the sequence TACGGACGGAAACT-GTTTTTTTTTTT (SEQ ID NO: 4).

30. The method of claim 27, wherein the fluorescent dye which is linked to the third oligonucleotide is 6-(fluorescein-6-carboxamido) hexanoate.

31. The method of claim 27, wherein the primary amine group which is linked to the third oligonucleotide is a C-7 amine.

32. The method of claim 27, wherein the third oligonucleotide is immobilized on a solid support.

33. The method of claim 32, wherein the solid support is a glass bead.

34. The method of claim 27, wherein the third oligonucleotide (1) is immobilized; (2) comprises the sequence TACG-GACGGAAACTGTTTTTTTTTTT (SEQ ID NO:4); (3) is linked to 6-(fluorescein-6-carboxamido) hexanoate at its 5' terminus, and (4) is linked to a C-7 amine at its 3' terminus.

35. The method of claim 27, wherein the fluorescent dye which is linked to the primer in step (B) (2) Texas red.

36. The method of claim 27, wherein the sample is a serum sample.

* * * * *